United States Patent [19]

Thorpe et al.

[11] Patent Number: 5,395,755
[45] Date of Patent: Mar. 7, 1995

[54] ANTIOXIDANT ASSAY

[75] Inventors: Gary H. G. H. Thorpe, Handsworth; Thomas P. Whitehead, Leamington Spa, both of England

[73] Assignee: British Technology Group Limited, London, England

[21] Appl. No.: 949,518
[22] PCT Filed: Jun. 11, 1991
[86] PCT No.: PCT/GB91/00931
§ 371 Date: Nov. 25, 1992
§ 102(e) Date: Nov. 25, 1992
[87] PCT Pub. No.: WO91/19979
PCT Pub. Date: Dec. 26, 1991

[30] Foreign Application Priority Data

Jun. 12, 1990 [GB] United Kingdom ............... 9013141.8
Sep. 5, 1990 [GB] United Kingdom ................. 9019376

[51] Int. Cl.$^6$ .............................................. C12Q 1/28
[52] U.S. Cl. ........................................ 435/28; 435/79; 435/810; 435/968; 436/172
[58] Field of Search ................. 435/7.9, 28, 810, 968; 436/172

[56] References Cited

U.S. PATENT DOCUMENTS

| | | | |
|---|---|---|---|
| 4,675,281 | 6/1987 | Lands et al. | 435/4 |
| 4,729,950 | 3/1988 | Kricka et al. | 435/28 |
| 4,828,983 | 5/1989 | McClune | 435/7 |
| 4,835,101 | 5/1989 | Kao et al. | 435/28 |
| 4,842,997 | 6/1989 | Carter et al. | 435/6 |
| 4,933,276 | 6/1990 | Baret | 435/7 |
| 5,043,266 | 8/1991 | Dewar et al. | 435/7.9 |
| 5,108,893 | 4/1992 | Baret | 435/6 |

FOREIGN PATENT DOCUMENTS

| | | |
|---|---|---|
| 116454 | 8/1984 | European Pat. Off. |
| 249618A3 | 9/1987 | Germany . |
| 2205945A | 12/1988 | United Kingdom . |
| 745924 | 7/1980 | U.S.S.R. |
| 1045127 | 9/1983 | U.S.S.R. |
| 1294344 | 3/1987 | U.S.S.R. |
| 1513405 | 10/1989 | U.S.S.R. |
| 1532869 | 12/1989 | U.S.S.R. |
| 0087959 | 9/1983 | WIPO . |
| WO90/07115 | 6/1990 | WIPO . |

OTHER PUBLICATIONS

Rao et al "Specificity of oxygen radical scavenger . . . " Biochemical & Biophysical Res. Comm. vol. 150 No. 1, (15 Jan. 1988), pp. 39–44.

Sevanian et al., "Conservation of Vitamin C by uric acid in blood", Journal of Free Radicals in Biology & Medicine 1, 117–124 (1985).

Wayner et al., "The relative contributions of Vitamin E, urate, ascorbate . . . ", Biochimica et Biophysica Acta 924, 408–419 (1987).

Radi et al., "Comparison of the effects of superoxide dismutase . . . ", Biochimica et Biophysica Acta 994, 89–93 (1989).

Archer et al., "Detection of activated $O_2$ species in vitro and in rat lungs . . . " J. Appl. Physiol. 67, 1912–1921 (1989).

Jones and Scowen, "Kinetics and mechanism of catalysis by ferrihaems . . . ", Photochemistry and Photobiology 45, 283≧289 (1987).

Asayama et al., "Chemiluminescence as an Index of Drug-induced Free Radical Production in Pancreatic Islets", Diabetes 33, 160–163 (1984).

Popov et al., "Photochemiluminescent detection of antiradical activity . . . " Biomed Biochim. Acta 46, 775–779 (1987).

Dormandy, "Free radical pathology and medicine", J. Royal College of Physicians of London 23, 221–227 (1989).

Kahl et al., "Detection of oxygen activation . . . ", Archives of Toxicology 60, 158–162 (1987).

(List continued on next page.)

Primary Examiner—James C. Housel
Assistant Examiner—Harold Y. Pyon
Attorney, Agent, or Firm—Nixon & Vanderhye

[57] ABSTRACT

A method of assay of antioxidant activity of a biological fluid, which comprises monitoring the change exerted by the sample on a progressing luminescent reaction.

11 Claims, 5 Drawing Sheets

OTHER PUBLICATIONS

Frew and Jones, "Assay of some chemically important reductants by a chemiluminescence-delay technique", Analytical Letters 18, 1579–1592 (1985).

Jones et al., "Inorganic fireflies-a chemiluminescent clock reaction", J. Chemical Education 64, 70–71 (1987).

Majkic ∝ Singh et al., "Evaluation of the enzymatic assay of serum uric acid . . . " Ann. Clin. Biochem. 21, 504–509 (1984).

Wong and Salin, "Quenching of peroxidised luminol chemiluminescence by reduced pyridine nucleotides", Photochemistry and Photobiology 33, 737–740 (1981).

Cash et al., "A Chemiluminescence Study of the Oxidation of Vegetable Oils . . . ", J. Sci. Food Agric. 43, 277–287 (1988).

Suematsu et al., "Increased respiratory burst of leukocytes in inflammatory bowel diseases . . . ", J. Clin. Lab. Immunol. 24, 125–128 (1987).

Descamps-Latscha et al., "Chemiluminescence in Microamounts of whole blood . . . ", Ann. Immunol. (Inst. Pasteur) 133C, 349–364 (1982).

Slawinska and Slasinski, "Chemiluminescent Analysis in Biochemistry", Post Biochem 23, 445–473 (1977) with partial translation.

Krol et al., "Anti-oxidant property of ethanolic extract of Propolis (EEP) . . . ", Biochemistry International 21 (4), 593–597 (Aug. 1990).

Metsa-Ketela "Luminescent assay for total peroxy radical-trapping capability of plasma", Abstract 82, VIth Int. Symposium on Bioluminescence and Chemiluminescence, University of Cambridge (England) 10–13 Sep., 1990.

Candy et al., "Kinetics and Mechanism of a Chemiluminescent Clock Reaction . . . ", J. Chem. Soc. Perkin Trans. 2, 1385–1388 (1990).

Kharfuf et al., "Mechanisms of the antioxidative action of screened phenols . . . ", a translation from Byulletin Eksperimental'noi Biologii i Meditsing 110, (11), 480–483 (1990).

Whitehead et al., "Enhanced chemiluminescent assay for antioxidant capacity in biological fluids", Analytica Chimica Acta, 266, 265–267 (1992).

Popov et al, The influence of ascorbic acid in the preservation solution on the antioxidative potential of blood plasma during liver transplantation in minipigs 1989, Inst. Med. Immunol., Humboldt-Univ. (see abstract).

ANTIOXIDANT ASSAY

BACKGROUND OF THE INVENTION

1. Field of Invention

This invention relates to a method of assaying the antioxidant capacity of a sample, especially mammalian serum or plasma, using a luminescent reaction.

2. Description of Prior Art

Cellular damage by free-radicals particularly oxyradicals is generally believed to be a significant factor in many diseases including heart disease, cancer, rheumatoid arthritis and the aging process itself (Wayner, D.D.M. et al, Biochim. et Biophys. Acta (1987), 924, 408–419). It is known that blood including both cells and plasma has mechanisms to defend the organism against free-radicals. It is postulated that in some disease states these mechanisms are disturbed either by excessive production of free-radicals or by a decrease in the defence mechanism.

The mechanism is recognised as complex involving several substances capable of "scavenging". Such substances include urate, ascorbate, vitamin E, and various proteins including some containing selenium. There is experimental evidence (Sevanian, A. et al, J. Free Rad in Biol. Med. (1985), 1, 117–124), that the substances involved act in a combined manner to give a total antioxidant property to the system. It can be shown for example, that urate protects ascorbate (Sevanian et al, as above) and ascorbate protects other peroxyl radical scavengers (Frei et al. PNAS 86 6377 (1989)).

To ascertain the total antioxidant capacity of blood plasma or serum, it is inconvenient, if not impossible, to determine the concentration of all the participating scavengers. Furthermore the total antioxidant capacity appears to be greater than the sum of those of all the participating scavengers (Sevanian et al., as above).

A suitable method for assaying rapidly and simply the total antioxidant capacity of biological fluids especially blood plasma or serum, would be of benefit as a diagnostic or patient monitoring tool.

A method for determining the total peroxyl radical trapping antioxidant activity of human blood plasma has been published (Wayner et al, Biochem. et Biophys. Acta (1987), 924, 408–419). The method is based on the discovery that peroxidation of aqueous dispersions of oxidizable organic compounds can be reproducibly initiated by thermal decomposition of the water-soluble azo compound 2,2'-azo-bis(2-amidinopropane hydrochloride (ABAP). At 37° C. ABAP decomposes thermally to yield useful quantities of peroxyl radicals at a known and constant rate. The total peroxyl radical trapping antioxidant parameter (TRAP) is determined from the length of time a plasma sample resists peroxidation as measured by the rate of uptake of oxygen when subjected to attack by peroxyl radicals. Changes can be monitored by a pressure transducer or a modified oxygen electrode.

Although it has yielded useful information on the role of various constituents in plasma as antioxidants, this electrochemical method is complex and lengthy, taking up to 90 minutes per assay, which can only be done one at a time. It requires equipment which is not always available, is not easily operable and has to be cleaned after each assay. Accordingly, there is still a need for a suitable alternative, that is convenient to use and is capable of providing a total antioxidant capacity as well as information regarding the contribution of individual antioxidant components.

Further prior art is mentioned after the "Summary of the Invention", without which its context would not be clear.

SUMMARY OF THE INVENTION

It has now been found that when a test sample is added to a progressing luminescent reaction, the antioxidants present in the sample cause a transient reduction in the observed luminescence (measured light output). The level of luminescence recovers close to its initial level after a short time. This time period, during which the observed luminescence is reduced, provides an index as to the capacity of the antioxidants in the test sample.

Thus, the antioxidant capacity of a given sample can be assayed (determined) utilizing a luminescent reaction.

The term "assay" or "determination" as used herein, includes qualitative, semi-quantitative and quantitative indications, assessments, estimations and measurements.

In a first embodiment of the invention the sample is added to the progressing luminescent reaction when the level of luminescence is substantially constant, that is the level of luminescence after rising to a maximum level, plateaus, remaining at substantially the maximum level or decreasing at a moderate rate, typically of up to 0.6% per minute. It will be appreciated that the nature of this plateau can vary considerably according to the reactants chosen, but one skilled in the art will have no difficulty in recognising a plateau since such luminescent reactions are known per se.

In an alternative embodiment of the invention the sample is added to the progressing luminescent reaction before it reaches the said substantially constant level, but is within 10% of the maximum.

The addition of the sample to the progressing luminescent reaction results in a sudden drop in the level of luminescence, which is followed by a recovery towards the said substantially constant level. The time interval between the time when the sample is added and a predetermined level of recovery is measured and provides an index as to the antioxidant capacity of the sample. The level of luminescence recovers to a second substantially constant level. This second level may be lower than the original said substantially constant level. The level of recovery of luminescence at a given time interval from the time when the sample is added can be measured and compared to the level of luminescence at the time when the sample was added. As is discussed hereinafter, assays can be based on other time periods during the reaction.

Advantages of the present invention include the following: 1) the assay can be carried out in a single step for each sample, i.e. there is no series of separate reactions required to obtain the result; 2) the assay normally requires no addition of exogenous antioxidant and subsequent comparison to a standard curve of pure antioxidant solutions, 3) the assay comprises a "real time" measurement which enables the level of observed luminescence before the addition of the test sample to be compared with the level observed after the transient depression; the comparison of these levels and/or the shape of the curve defining the transient depression provides further information regarding the nature of the antioxidants present in the test sample, and 4) the apparatus required is relatively simple, easy to maintain and permits several assays to be carried out simultaneously.

The invention is of foremost applicability to oxygen-dependent chemiluminescent reactions, especially peroxidase-catalysed and especially such reactions which will provide a high and substantially constant rate of photon production or level of light output as described hereinbefore. To meet such a requirement an enhancer of the luminescent reaction will often be required.

In a further embodiment of the invention, the antioxidant contribution of any specific or particular classes of antioxidants known or suspected to be present in a sample may be determined by comparing the antioxidant capacity of the sample before and after removal of that specific antioxidant. Thus the antioxidant contributions of proteins, ascorbic acid and uric acid for example may be determined.

The invention also includes a kit for carrying out the assay comprising a luminescent substrate and an antioxidant (for carrying out standardisations). Other reagents required for the luminescent reaction can, of course, be included in such a kit.

DESCRIPTION OF ADDITIONAL PRIOR ART

It is a known feature of antioxidants that they will depress luminescence observed from a number of different chemiluminescent sources (Radi et al, Biochimica et Biophysica Acta (1989), 994, 89-93). This property has been used in an attempt to determine which radicals are preferably "mopped up" by which antioxidant (Rao et al, Biochem. and Biophys. Res. Commun. (1988), 150, (1), 39-44) and also to compare the efficiency of different food antioxidants (kahl et al, Arch. Toxicol. (1987), 60, 158-162). It has further been developed to assay superoxide dismutase (see Popov et al., Biomed. Biochim. Acta (1987), 46, (11), 775-9). Frew et al. (Anal. Lett. (1985) 18 (B 13) 1579-1592) have developed a chemiluminescent delay technique for the assay of reductants. All the components for the ferrihaem catalysed oxidation of luminol were mixed together with the reductant prior to the addition of hydrogen peroxide which initiated the chemiluminescent reaction. The time delay before any chemiluminescence was observed was taken as an index of the amount of reductant originally added. This relationship between the time delay and concentration of reductant was linear over a limited range of reductant concentrations. Wong et al. (Photochem. & Photobiol. (1981) 33 737-740) found a linear relationship between time delay before observation of chemiluminescence and concentration of reduced pyridine nucleotides, for example NADH and NADPH. They used a luminol-HRP unenhanced chemiluminescent reaction, and mixed the reduced nucleotides with the reactants prior to the initiation of the reaction by hydrogen peroxide. They also observed that the maximum level of light output was reduced when higher concentrations of reduced nucleotides were added. This quenching of light output was also observed when using other reductants such as ascorbic acid, dithionite, ferrocyanide and cysteine. Neither of these two last-mentioned papers discuss further experimentation or investigation of the observed phenomena and no further applications of these observations were proposed. Moreover, there has been no report of this method being a possible means by which to measure the total antioxidant capacity of blood serum or plasma.

BRIEF DESCRIPTION OF THE ACCOMPANYING DRAWINGS

FIGS. 1-12 are graphs of light emission from a luminescent reaction, to which different samples have been added, plotted against time.

DESCRIPTION OF THE PREFERRED EMBODIMENTS

The oxygen-providing component of the luminescent reaction need not be molecular oxygen but can be hydrogen peroxide or a perborate, for example.

One suitable chemiluminescent reaction which exhibits a relatively constant photon emission is one in which the reaction takes place between a peroxidase, an oxidant and a dihydrophthalazinedione (DPD), in the presence of an enhancer. Such chemiluminescent reactions are described in European Patents Nos. 87,959 and 116,454 and in U.K. Patent 2162946 and U.K. Patent Application No. 8814148.6 (Publication No. 2205945A) and any of these can be used in the context of the present invention.

For the purposes of the present invention a preferred DPD is luminol or isoluminol, a preferred oxidant is hydrogen peroxide and preferred enhancers are para-iodophenol, para-hydroxy cinnamic acid or para-imidazol-1-ylphenol, most preferably p-iodophenol. These enhancers give a high and relatively constant rate of light emission over an extended period and may be used as a "benchmark" of preferred maximum levels of high output for use in the context of the invention, regardless of the nature of the enhancer or other reagents employed. Other enhancers that are of use in the present invention include 2-cyano-6-hydroxybenzothiazole, 1-bromo-2-naphthol, para-phenyl-phenol and N,N,N',N'-tetramethyl-benzidine. A preferred peroxidase enzyme is horseradish peroxidase (HRP).

The chemiluminescent reactions described above are only intended to be representative of the many suitable luminescent reactions that may be known to those skilled in the art. Many other known chemiluminescent reactions or variations thereof are likely to be found useful for the present purposes and can be investigated by simple experimentation.

The changes in light emission may be monitored using a conventional photomultiplier tube luminometer with a recorder. For simple qualitative studies a photographic film or even visual observation may be suitable. A further advantage of the present invention is that because of the relatively high intensity of light emission the assay may be monitored using a "hand held" battery operated luminometer from which readings of photon output can be made every 30 seconds or less.

The assay used in the present invention is of use with many different types of samples. Thus it is applicable to biological fluids including mammalian serum or blood plasma, cerebrospinal fluid, synovial fluid or saliva. The assay is of further use in assaying the antioxidant capacity of tissues, cells or other materials such as foodstuffs and oils. Synovial fluid will provide useful information in the diagnosis and/or prognosis of arthritic or rheumatic disorders whereas CSF will provide possible implications of free radical induced nerve degeneration in the brain and spinal cord, and any possible role they may have in neural inflammation in diseased states or after injury. Crevicular fluid may provide an indication as to the presence of inflammation in the tooth root or gum.

In a further embodiment the invention can be used to determine the contribution of specific or particular classes of antioxidants known or suspected to be present in a sample, by comparing the antioxidant capacity as measured by the method of the invention before and after the specific or particular classes of antioxidants have been removed or extracted.

Thus, the antioxidant contribution of the proteins contained within a sample may be determined by comparing the antioxidant capacity of the sample before and after the proteins have been removed. Protein removal may be achieved by methods well known in the art including alcohol precipitation or filtration with centrifugation through a molecular filter.

Similarly, the antioxidant contribution of other antioxidants may be determined using methods known in the art to remove them from the sample, for example using ascorbate oxidase to remove ascorbic acid. A further application of the invention is in monitoring the effectiveness of free-radical scavenging drugs. Thus, after administration of such a drug, the antioxidant capacity can be monitored to provide information on the rate of recovery. This is of importance for example, with the radical scavenging drug Captopril.

Similarly, the invention has application in monitoring the progress of patients suffering from the large number of diseases and infections that cause a change in the balance of free-radicals and antioxidants in body fluids.

Furthermore, the invention can provide a non-invasive indication of the antioxidant capacity as fluids such as tears and saliva are also sensitive in this assay.

FIG. 1 of the drawings illustrates how the light intensity of the luminescent reaction can be affected by addition of sample, whilst the reaction is progressing, light intensity being plotted against time. Referring to FIG. 1, the distances marked have the following meanings:

"a" is the time from addition of sample to the trough;
"b" is the time of the trough (depression of light intensity);
"c" is the time from the end of the trough to the recovery of a relatively constant, although still diminished, light intensity.

The fall in light intensity (d) is the natural decay in the enhanced reaction, due to HRP inactivation etc. This is typically a decrease of no more than 2%, preferably no more than 1% and most preferably no more than 0.6% a minute. The fall in intensity (e) is predominantly due to effects such as protein quenching from the sample, although some further inactivation of HRP may occur. The light intensity (f) is that to which the solution returns after exposure to the sample.

The time period of (a)+(b)+(c) or (b)+(c) is probably the most significant quantitative measurement, although the area (g) could equally be useful. Time intervals (a) alone, (b) alone and (c) alone, and the shape of these curves are also useful for quantitative and qualitative assessment of the type of antioxidant capacity.

It has been observed that the time periods (a), (b) and (c), the fall in intensity (e) and the shape of the rising phase of the curve over the time period (c) are representative of the contribution of certain "classes" of antioxidants. Thus, the length of the period (b) is believed to be due to low molecular weight antioxidants such as ascorbate, urate and vitamin E. The rising phase of the curve during the time period (c) is believed to be due to antioxidant properties of proteins and lipids, whereas the fall in intensity (e) is believed to be due predominantly to the amount of protein in the sample. Any or all of these properties can be used for medical diagnosis.

Alternatively, instead of measuring a time interval to the recovery of a relatively constant level of luminescence, it can be measured to some pre-determined level such as 50%–70% of either the initial value or of the final value. In another embodiment, the level of recovery of luminescence at a given time interval from the time when the sample is added is measured and compared to the level of luminescence at the time when the sample was added.

A particularly preferred kit for the assay of the invention comprises a DPD (e.g. luminol or isoluminol), an enhancer (e.g. iodophenol), a catalyst (e.g. peroxidase) and an antioxidant (e.g. ascorbic acid or a salt thereof). Preferably the kit further contains an oxidant (e.g. hydrogen peroxide) and buffer.

The following Examples illustrate the invention. "Amerlite" is a Registered Trade Mark of Amersham International PLC.

EXAMPLE 1

"Amerlite" signal reagent was obtained from Amersham International PLC and prepared according to the manufacturer's instructions. Similar results were obtained using a solution of luminol (as luminescent substrate), p-iodophenol (enhancer), and hydrogen peroxide in Tris buffer, pH 8.5.

Ten $\mu$l of a horseradish peroxidase-antibody conjugate (1:1000 dilution) was added to 1 ml of the luminescent substrate and the light intensity and kinetics recorded using a luminometer and chart recorder. This was left for 2 minutes, or until a plateau of light emission was observed. The cuvette containing the glowing solution was then removed from the luminometer, and an aliquot of fresh serum (typically 1 to 10 $\mu$l) added to the cuvette. This was immediately reintroduced into the luminometer and the kinetics of light emission monitored and compared to the light emission before sample addition. Similar experiments were performed with the fresh serum replaced by either serum which had been stored at room temperature and exposed to daylight for 3 days (with consequently reduced antioxidant capacity), or solutions of ascorbic acid or uric acid as antioxidants in 0.1M Tris buffer, pH 8.5.

It was shown that storage of serum reduces the antioxidant properties.

EXAMPLE 2

Use of Antioxidant Assay on Different Biological Fluids

"Amerlite" signal reagent was prepared as described in the manufacturer's instructions and a 1 in 10 dilution of this was used, hereinafter described as the signal reagent. 60 $\mu$l of Amerlite HRP anti-IgG conjugate (as a source of HRP) was added to 20 ml of distilled water for use in the assay. 1 ml of signal reagent in water was placed in a cuvette to be used in the luminometer. 20 $\mu$l of the working HRP conjugate was added. This was placed in the luminometer for 2 minutes or until a substantially constant level of photon output was observed. When a constant level was attained, 20 μl of test sample was added and that moment taken as zero time. The reaction was allowed to continue for about 8 minutes. Measurements were made on a bench luminometer (using a photomultiplier tube and photocurrent measurements). In further Examples where this procedure was repeated, 20 μl Amerlite HRP conjugate was added to 20 ml distilled water for use in the assay and the 1 ml of signal reagent in water, comprised 100 μl reagent with 900 μl water.

All the test samples a) serum; b) CSF; and c) synovial fluid were diluted 1 in 10 in distilled water before being added to the progressing luminescent reaction.

Figure 6:
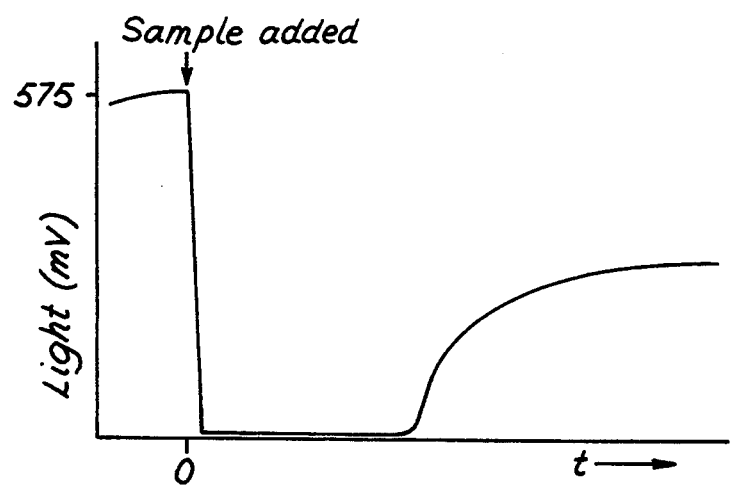
Figure 4:
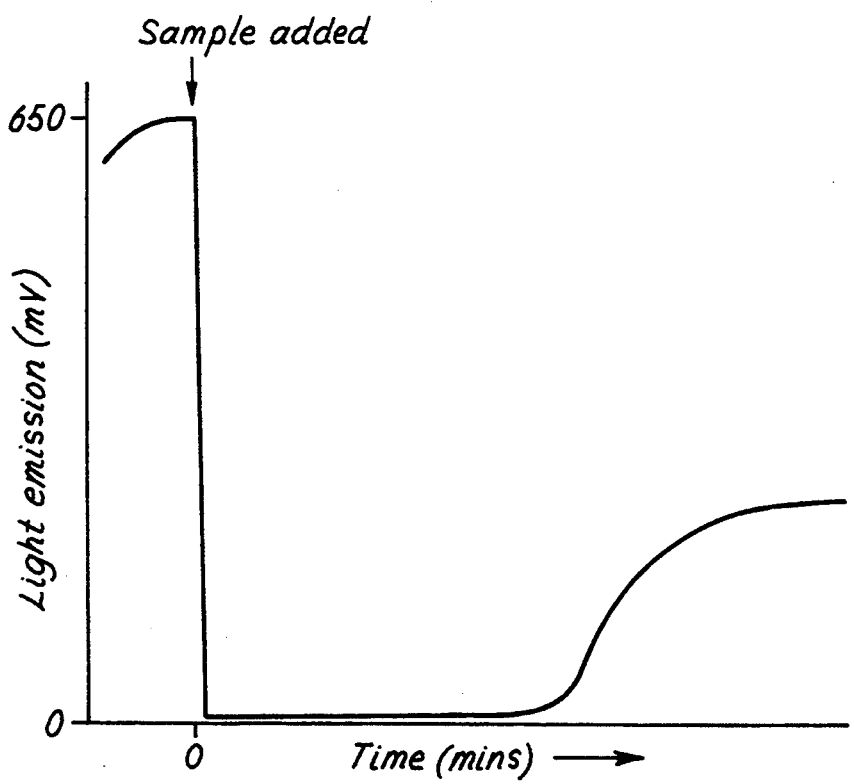
Figure 5:
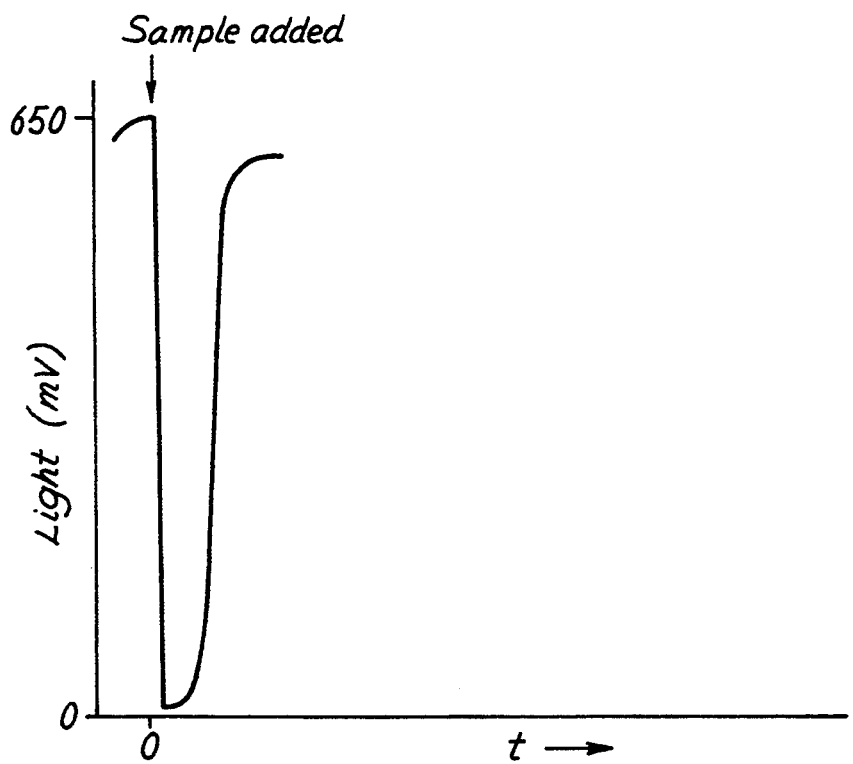

FIGS. 4 to 6 show the effect of each of the test samples a) to c) respectively on a progressing luminescent reaction. In all cases light output is plotted on the ordinate and time on the abscissa.

For all test samples the level of luminescence did not return to its former level after the addition of the test sample. This is probably due to protein quenching and is hence absent when using pure ascorbic acid.

EXAMPLE 3

Effect of Various Antioxidant Components of Blood on the Antioxidant Assay

The procedure of Example 2 was repeated using solutions of ascorbic acid, uric acid and human serum albumin.

The test samples were added at the following concentrations: a) ascorbic acid 1.6 nmols, 0.3 nmols, 0.16 nmols; b) uric acid 2.0 nmols, 1.0 nmols, 0.7 nmols; c) albumin 12 nmols, 6 nmols, 3 nmols and 2 nmols.

Figure 7:
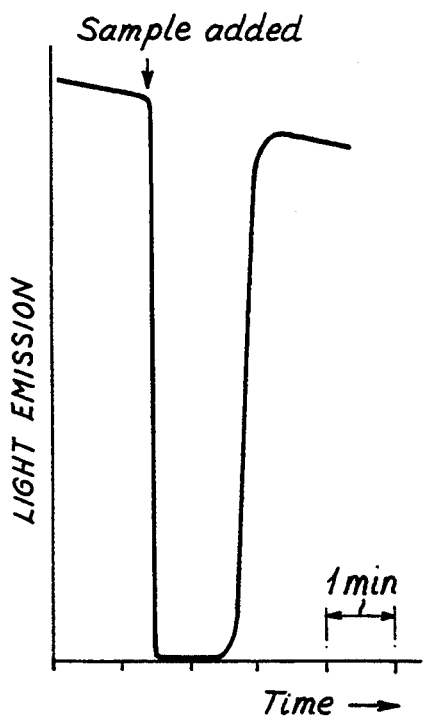
Figure 8:
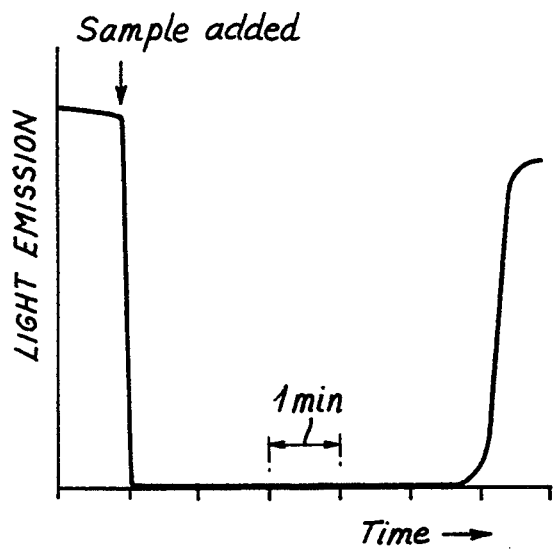
Figure 9:
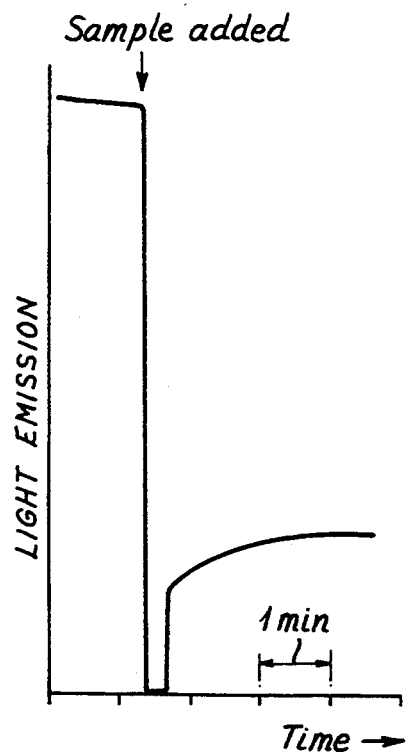

FIGS. 7 to 9 show the effect of ascorbic acid 0.3 nmols uric acid 1.0 nmols and albumin 3.0 nmols respectively.

Figure 1:
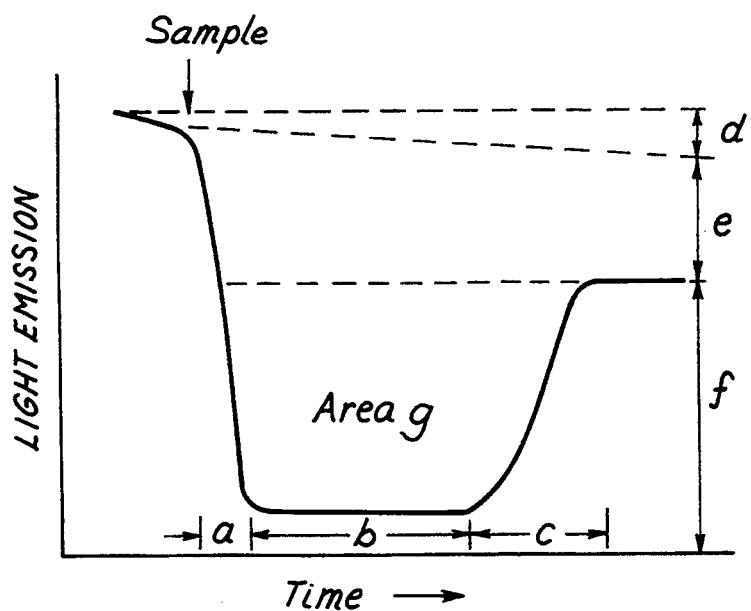

Table 1 shows the time in seconds for the period (b)+(c) (see FIG. 1) and the degree of recovery as expressed by % of the initial level to which the luminescence recovered. As can be seen from the Table, at higher concentrations of low molecular weight antioxidants (ascorbic acid, uric acid), the time taken to reach a "recovered" state increased, whilst the degree to which recovery occurs remained largely unchanged. The converse was true for protein, e.g. for albumin at higher concentrations the trough period was not dramatically altered, but the degree of recovery became depressed.

TABLE 1

| Sample | (nmols) | Time Period (b) + (c) in secs. | % Recovery |
|---|---|---|---|
| Ascorbic Acid | 0.16 | 36 | 93 |
| | 0.30 | 60 | 95 |
| | 1.60 | 360 | 87 |
| Uric Acid | 0.70 | 220 | 90 |
| | 1.00 | 312 | 92 |
| | 2.00 | 645 | 89 |
| Albumin | 2.00 | 15 (approx.) | 40 |
| | 3.00 | 15 (approx.) | 25 |
| | 6.00 | 15 (approx.) | 11 |
| | 12.00 | 15 (approx.) | <1 |

EXAMPLE 4

Antioxidant Capacity in Diseased States

The procedure of Example 2 was repeated using sera prepared from patients suffering from a) acute pancreatitis, b) rheumatoid arthritis and c) renal failure. These samples were diluted 1:10 and added to the progressing chemiluminescent reaction.

Figure 2:
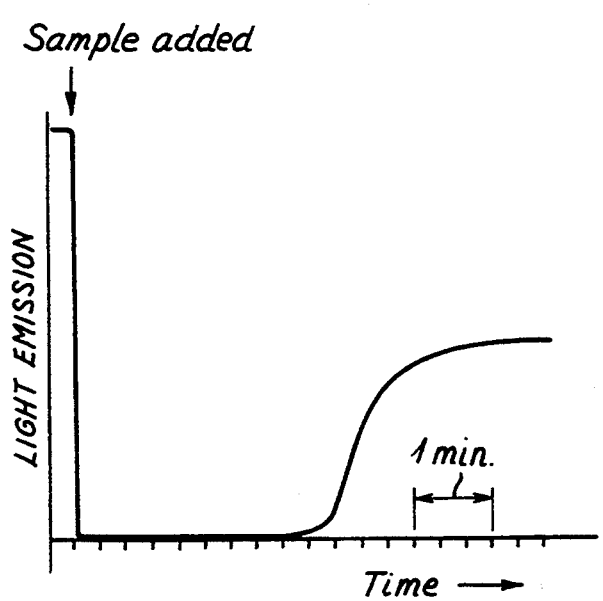
FIG. 2 shows the transient reduction in chemiluminescence due to the addition of fresh serum. This lasted for about 190 seconds, after which the light output began to return to about 50% of the original value.
Figure 3:
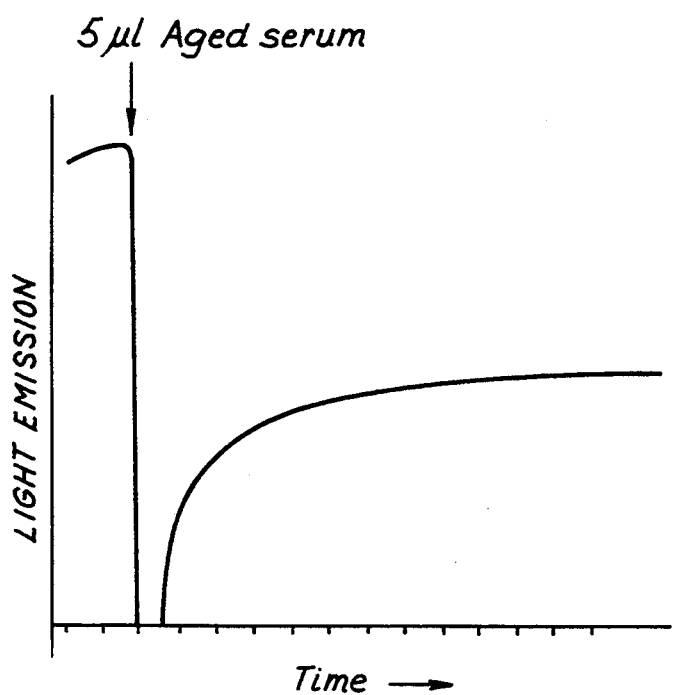
FIG. 3 shows the similar effect on light output by addition of stored serum. Note that the time period of the depression is shorter than for fresh serum.
Figure 10:
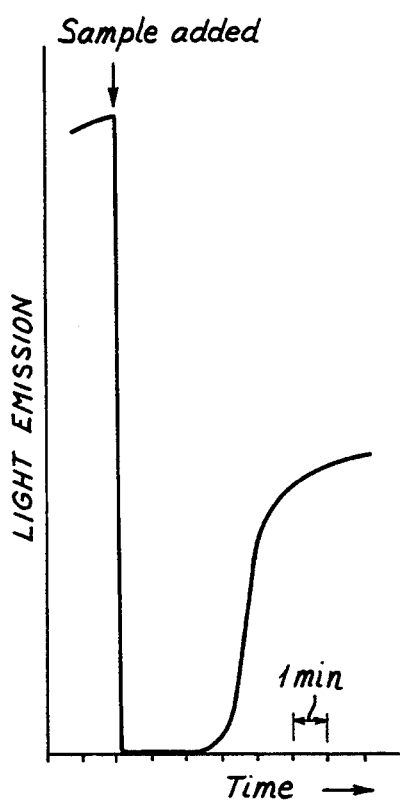
Figure 11:
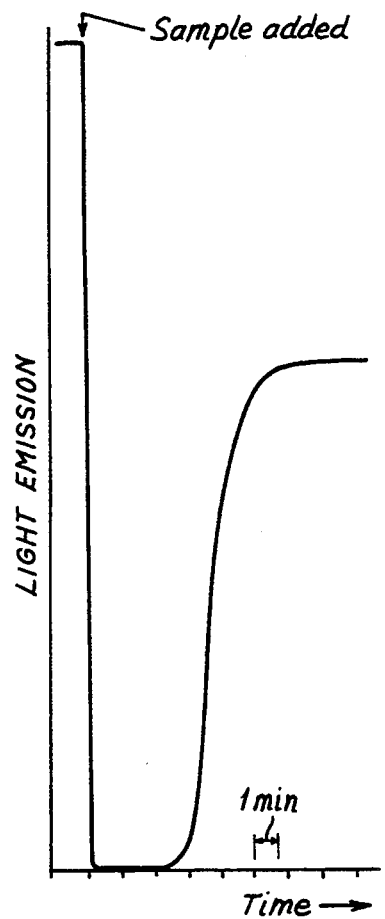
Figure 12:
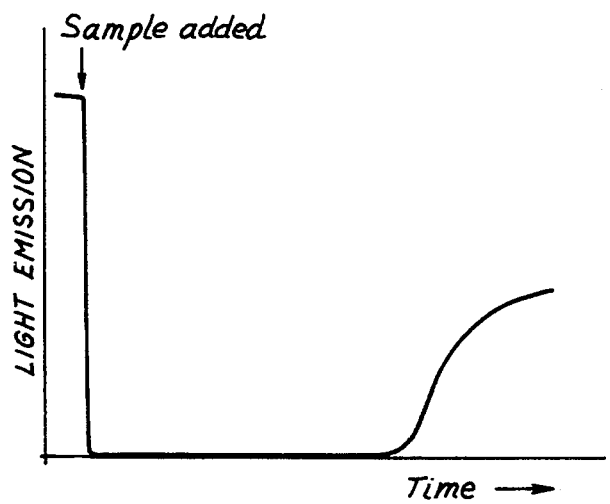

FIGS. 10 to 12 show the effect of each of the samples. By comparison with FIG. 2 (serum from a healthy donor) it can be seen that antioxidant capacity was reduced considerably in the samples from the pancreatitus and rheumatoid arthritis, FIGS. 10 and 11. In the case of the patient with renal failure, FIG. 12, the antioxidant capacity was increased as the kidneys failed to "clear" the body of metabolites such as urate.

EXAMPLE 5

Substrates and Enhancers Suitable for Use in the Antioxidant Assay

In addition to the chemiluminescent reaction used in the earlier examples, the following other substrates and enhancers for HRP-catalysed chemiluminescent reactions have been shown to be of use in the present invention.

| Substrate | Enhancer |
|---|---|
| Luminol | 2-cyano-6-hydroxybenzothiazole |
| Luminol | 1-bromo-2-naphthol |
| Luminol | para-phenyl-phenol |
| Luminol | N,N,N',N'-tetramethylbenzidine |
| N-(6-aminohexyl-N-ethyl-isoluminol (AHEI) | para-iodophenol |
| AHEI | 2-cyano-6-hydroxybenzothiazole |
| AHEI | 1-bromo-2-naphthol |
| AHEI | para-phenyl-phenol |
| AHEI | N,N,N'N'-tetramethylbenzidine |

EXAMPLE 6

Determination of Contributing Antioxidants to Total Antioxidant Capacity

The procedure of Example 2 was repeated using a range of concentrations of TROLOX (6-hydroxy-2,5,7,8-tetramethylchroman-2-carboxylic acid : Aldrich), fresh serum and the products of the following treatments.

a) A sample of the fresh serum was centrifuged through a protein filter. Such a filter restricts all substances with a molecular weight greater than 10,000. The filtrate (sample (a)) was assayed to determine the contribution of the removed proteins on the total antioxidant capacity.

b) A portion of the filtrate (sample (a)) was treated with ascorbate oxidase on a solid support. The treated filtrate (sample (b)) was assayed to determine the contribution of ascorbate on the total antioxidant capacity.

Table 2 below shows the antioxidant capacity of fresh serum, sample (a) and sample (b) as expressed in μmols/l equivalent of TROLOX. Thus, the protein removed in step a) made a contribution to the total antioxidant capacity equivalent to 311 μmol/l TROLOX. Similarly, the ascorbate contributed an equivalent of 121 μmol/l TROLOX to the total antioxidant capacity of the serum.

TABLE 2

| Sample | Antioxidant Capacity (μmol/l equivalent of TROLOX) |
|---|---|
| fresh serum | 800 |
| sample (a) | 489 |
| sample (b) | 368 |

Step a) was repeated by shaking 100 μl of serum in 900 μl ethyl alcohol and assaying 20 μl of the resultant supernatant obtained after centrifuging the mixture. This deproteinated serum provided an antioxidant capacity equivalent to 245 μmol/l TROLOX. The difference in these two methods of protein removal is believed to be due to this latter method additionally removing lipid-soluble antioxidants.

We claim:

1. A method of assay of the antioxidant activity of a sample suspected of having such activity, which method comprises the steps of:
   (a) initiating a chemiluminescent reaction and allowing said reaction to progress, thereby to generate a level of luminescence, said level being selected from the group consisting of (i) a rising level between 90 to 100% of maximum, (ii) the maximum, and (iii) a post-maximum substantially constant plateau level;
   (b) adding said sample to said progressing chemiluminescent reaction, said sample causing said level of luminescence generated by said reaction to change when said sample has antioxidant activity;
   (c) monitoring said change in the level of luminescence; and
   (d) determining the antioxidant activity of said sample assayed by reference to that of samples of known antioxidant activity subjected to steps (a) to (c) above.

2. A method of determining the contribution of specific or particular classes of antioxidants in a sample, by comparing the antioxidant activity of the sample as measured by a method according to claim 1, before and after the specific or particular classes of antioxidants have been removed or extracted.

3. A method according to claim 1, in which the sample is a biological fluid.

4. A method according to claim 3, in which the biological fluid is mammalian serum or blood plasma, cerebrospinal fluid, synovial fluid or saliva.

5. A method according to claim 1, in which said chemiluminescent reaction is a peroxidase-catalyzed oxygen-dependent chemiluminescent reaction.

6. A method of assay according to claim 5, in which the chemiluminescent reaction is an enhanced chemiluminescent reaction.

7. A method according to claim 5, in which the chemiluminescent reaction comprises the reaction of a dihydrophthalazinedione (DPD) substrate.

8. A method according to claim 6, in which the enhancer is para-iodophenol.

9. A method according to claim 1, in which the time interval between the time when the sample is added and a predetermined level of luminescence is measured.

10. A method according to claim 1, in which said change monitored in step (c) is selected from the group consisting of
    (1) a time period during which the level of luminescence falls to a trough level;
    (2) a time period in which it remains at said trough level;
    (3) a time period in which it recovers partially to reach a new substantially constant plateau level of lower level of luminescence than the first-mentioned substantially constant plateau level; and
    (4) the shape of the curve during the time period (3).

11. A method according to claim 10, in which the chemiluminescent reaction is one in which the reaction takes place between a peroxidase, an oxidant and a dihydrophthalazinedione, in the presence of an enhancer and the sample is a biological fluid.

* * * * *